(12) United States Patent
Chambers et al.

(10) Patent No.: US 11,717,408 B2
(45) Date of Patent: Aug. 8, 2023

(54) IMPLANTABLE VALVE DEVICE

(71) Applicant: Cook Medical Technologies LLC, Bloomington, IN (US)

(72) Inventors: Sean Chambers, Bloomington, IN (US); Ram Paul, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 355 days.

(21) Appl. No.: 16/925,397

(22) Filed: Jul. 10, 2020

(65) Prior Publication Data

US 2020/0337844 A1    Oct. 29, 2020

Related U.S. Application Data

(63) Continuation of application No. 15/414,794, filed on Jan. 25, 2017, now Pat. No. 10,722,365, which is a continuation of application No. 12/252,918, filed on Oct. 16, 2008, now abandoned.

(60) Provisional application No. 60/980,770, filed on Oct. 17, 2007.

(51) Int. Cl.
*A61F 2/24*    (2006.01)

(52) U.S. Cl.
CPC .......... *A61F 2/2475* (2013.01); *A61F 2/2412* (2013.01); *A61F 2/2418* (2013.01); *A61F 2220/005* (2013.01); *A61F 2220/0008* (2013.01); *A61F 2220/0016* (2013.01); *A61F 2220/0058* (2013.01);

(Continued)

(58) Field of Classification Search
CPC ........ A61F 2/24; A61F 2/2412; A61F 2/2409; A61F 2/2418
See application file for complete search history.

(56) References Cited

U.S. PATENT DOCUMENTS

| 4,580,568 A | 4/1986 | Gianturco |
| 4,692,164 A | 9/1987 | Dzemeshkevich |
| 4,800,603 A | 1/1989 | Jaffe |

(Continued)

FOREIGN PATENT DOCUMENTS

| WO | 0067679 A1 | 11/2000 |
| WO | 2004096100 A1 | 11/2004 |

(Continued)

OTHER PUBLICATIONS

Garcia-Rinaldi, Raul, Implantation of Cryopreserved Allograft Pulmonary Monocusp Patch, Tex Heart Inst J 2002;29:92-9. Texas Heart Institute, Houston, TX, USA.

(Continued)

*Primary Examiner* — Seema Mathew
(74) *Attorney, Agent, or Firm* — MacMillan, Sobanski & Todd, LLC

(57) ABSTRACT

Valve devices, methods of making valve devices, and methods of treating various venous-related conditions, disorders and/or diseases are described. In one embodiment, a valve device includes an expandable support frame and a bioprosthetic valve attached to the support frame. The bioprosthetic valve comprises a leaflet and a contiguous wall portion harvested from a multi-leaflet xenogeneic valve. The contiguous wall portion includes the attachment region where the leaflets attaches to the vessel wall and, in some embodiments, includes the natural margins of attachment between the leaflet and vessel wall.

18 Claims, 4 Drawing Sheets

(52) U.S. Cl.
CPC . *A61F 2220/0075* (2013.01); *A61F 2240/001* (2013.01); *A61F 2250/0098* (2013.01)

(56) References Cited

U.S. PATENT DOCUMENTS

| | | | |
|---|---|---|---|
| 5,411,552 A | 5/1995 | Andersen | |
| 5,500,014 A | 3/1996 | Quijano | |
| 5,595,571 A | 1/1997 | Jaffe | |
| 5,720,777 A | 2/1998 | Jaffe | |
| 5,843,180 A | 12/1998 | Jaffe | |
| 5,843,181 A | 12/1998 | Jaffe | |
| 6,231,598 B1 | 5/2001 | Berry | |
| 6,299,635 B1 | 10/2001 | Frantzen | |
| 6,425,916 B1 | 7/2002 | Garrison | |
| 6,464,720 B2 | 10/2002 | Boatman | |
| 6,494,909 B2 | 12/2002 | Greenhalgh | |
| 6,508,833 B2 | 1/2003 | Pavcnik | |
| 7,569,071 B2 | 8/2009 | Haverkost et al. | |
| 10,058,424 B2* | 8/2018 | Cooper | A61F 2/2436 |
| 10,595,992 B2* | 3/2020 | Chambers | A61F 2/2412 |
| 11,583,396 B2* | 2/2023 | Chau | A61F 2/2445 |
| 2001/0039450 A1 | 11/2001 | Pavcnik | |
| 2003/0225446 A1 | 12/2003 | Hartley | |
| 2004/0019374 A1* | 1/2004 | Hojeibane | A61F 2/2412 |
| | | | 623/2.38 |
| 2004/0098079 A1 | 5/2004 | Hartley | |
| 2004/0186558 A1 | 9/2004 | Pavcnik | |
| 2004/0230287 A1 | 11/2004 | Hartley | |
| 2004/0260389 A1 | 12/2004 | Case | |
| 2005/0228486 A1 | 10/2005 | Case | |
| 2006/0004433 A1 | 1/2006 | Greenberg | |
| 2006/0178740 A1* | 8/2006 | Stacchino | A61F 2/848 |
| | | | 623/2.18 |
| 2006/0212111 A1* | 9/2006 | Case | A61F 2/2475 |
| | | | 623/1.24 |
| 2006/0259136 A1 | 11/2006 | Nguyen | |
| 2006/0282157 A1* | 12/2006 | Hill | A61B 90/39 |
| | | | 623/1.11 |
| 2007/0021826 A1* | 1/2007 | Case | A61F 2/2475 |
| | | | 623/1.15 |
| 2007/0038291 A1* | 2/2007 | Case | A61F 2/86 |
| | | | 623/1.16 |
| 2007/0067022 A1* | 3/2007 | Case | A61F 2/2418 |
| | | | 623/1.24 |
| 2007/0088424 A1 | 4/2007 | Greenberg | |
| 2007/0093887 A1* | 4/2007 | Case | A61F 2/2418 |
| | | | 623/2.18 |
| 2007/0100435 A1* | 5/2007 | Case | A61F 2/2418 |
| | | | 623/901 |
| 2007/0162103 A1 | 7/2007 | Case | |
| 2007/0288086 A1* | 12/2007 | Kalmann | A61F 2/2418 |
| | | | 623/1.1 |
| 2007/0288087 A1* | 12/2007 | Fearnot | A61F 2/2418 |
| | | | 623/2.18 |
| 2008/0071368 A1* | 3/2008 | Tuval | A61F 2/2469 |
| | | | 623/2.17 |
| 2008/0215144 A1* | 9/2008 | Ryan | A61F 2/2418 |
| | | | 623/2.18 |
| 2008/0221656 A1 | 9/2008 | Hartley | |
| 2009/0105813 A1 | 4/2009 | Chambers et al. | |
| 2009/0132037 A1* | 5/2009 | Hoffman | A61F 2/2418 |
| | | | 623/2.38 |
| 2010/0114296 A1* | 5/2010 | Case | A61F 2/2475 |
| | | | 623/1.16 |
| 2012/0310328 A1* | 12/2012 | Olson | A61F 2/2469 |
| | | | 623/1.26 |
| 2015/0359629 A1* | 12/2015 | Ganesan | A61F 2/2436 |
| | | | 623/2.14 |
| 2021/0228342 A1* | 7/2021 | Levi | A61F 2/2409 |

FOREIGN PATENT DOCUMENTS

| | | |
|---|---|---|
| WO | 2007013108 A1 | 2/2007 |
| WO | 2007123658 A1 | 11/2007 |

OTHER PUBLICATIONS

Lurie, Fedor, Mechanism of Venous Valve Closure and Role of the Valve in Circulation: A New Concept, J Vasc Surg 2003;38:955-61. Elsevier, Amsterdam, The Netherlands.

Lurie, Fedor, The Mechanism of Venous Valve Closure in Normal Physiologic Conditions, J Vasc Surg 2002;35:713-7. Elsevier, Amsterdam, The Netherlands.

Garcia-Rinaldi, Raul, Femoral Vein Valve Incompetence: Treatment with a Xenograft Monocusp Patch, J Vasc Surg 1986; 3:932-5. Elsevier, Amsterdam, The Netherlands.

Van Bemmelen, Paul S. and Fedor Lurie, Letters to the Editor, Regarding "The Mechanism of Venous Valve Closure in Normal Physiological Conditions", J Vasc Surg 2003;37(1) 237-38. Elsevier, Amsterdam, The Netherlands.

File history of U.S. Appl. No. 12/252,253 filed Oct. 15, 2008. Inventor, Norman Jaffe. Title, Biological Valve For Venous Valve Insufficiency.

File history of U.S. Appl. No. 12/789,176. Filing date, May 27, 2010. Inventor, Norman Jaffe. Title, Biological Valve For Venous Valve Insufficiency.

European Patent Office, Communication pursuant to Article 94(3) EPC for application No. 08839587.6 dated Aug. 21, 2013, p. 1-5.

* cited by examiner

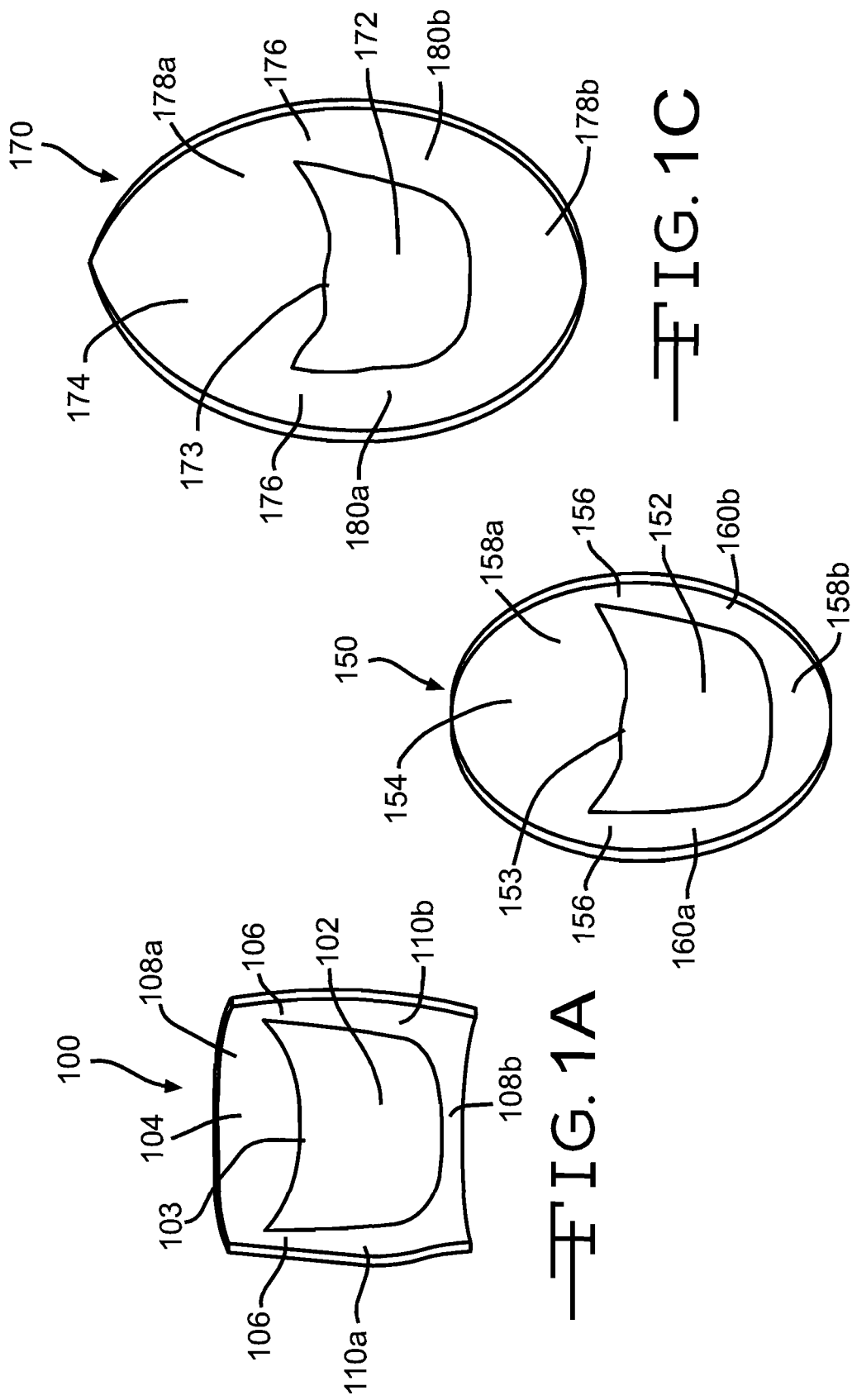

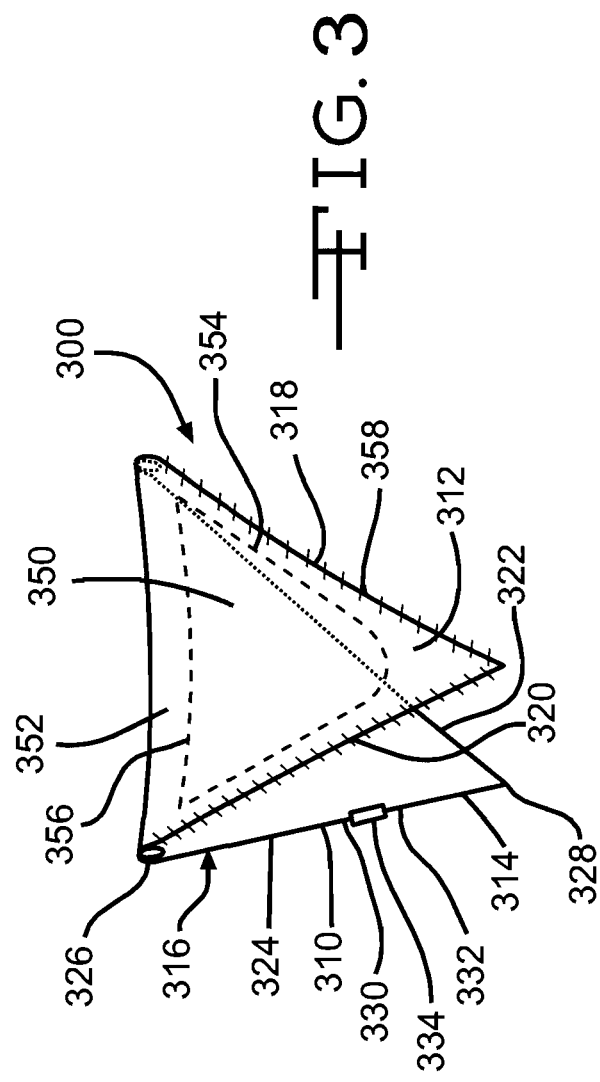
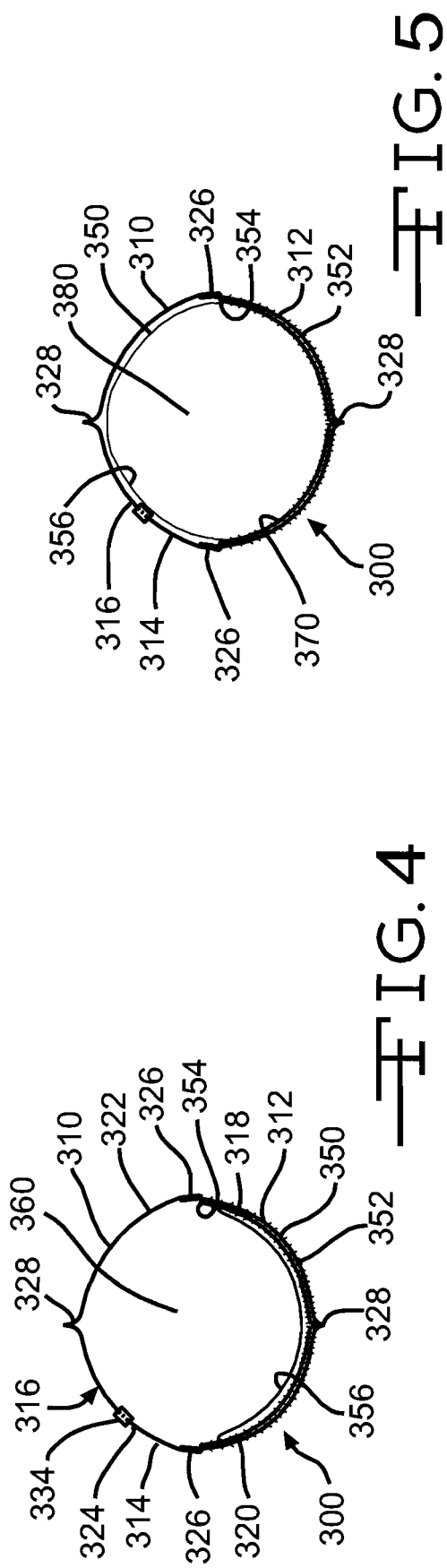

IMPLANTABLE VALVE DEVICE

CROSS REFERENCE TO RELATED APPLICATION

This application is a continuation of U.S. patent application Ser. No. 15/414,794, which was filed on Jan. 25, 2017, which is a continuation of U.S. patent application Ser. No. 12/252,918, which was filed on Oct. 16, 2008, which claims priority to U.S. Provisional Application No. 60/980,770, filed on Oct. 17, 2007. The entire contents of each of these related applications are hereby incorporated by reference into this disclosure.

FIELD

The disclosure relates generally to the field of implantable medical devices useful in the regulation of fluid flow through a body vessel. Particular embodiments relating to venous valve devices, the methods of making such devices, and methods of treating various venous-related conditions, disorders and/or diseases, including venous insufficiency are described in detail.

BACKGROUND

Many vessels in animal bodies transport fluids from one bodily location to another. Typically, fluid flows in a unidirectional manner along the length of the vessel. Varying fluid pressures over time, however, can introduce a reverse flow direction in the vessel. In some vessels, such as mammalian veins, natural valves are positioned along the length of the vessel and act as one-way check valves that open to permit the flow of fluid in the desired direction and close to prevent fluid flow in a reverse direction, i.e., retrograde flow. The valves can change from an open position in response to a variety of circumstances, including changes in the cross-sectional shape of the vessel and the fluid pressure within the vessel.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the valve leaflets to close. Furthermore, the leaflets may become damaged, such as by formation of thrombus and scar tissue, which may also affect the ability of the valve leaflets to close. Once valves are damaged, venous valve insufficiency may be present, and can lead to discomfort and possibly ulcers in the legs and ankles.

Current treatments for venous valve insufficiency include the use of compression stockings that are placed around the leg of a patient in an effort to force the vessel walls radially inward to restore valve function and various surgical techniques in which valves are bypassed, eliminated, or replaced with autologous sections of veins having competent valves. Drastic ablation procedures, including laser ablation, vein ligation and stripping, are also frequently employed.

Other areas of medicine have benefitted greatly over recent years from the development of minimally invasive techniques and instruments for placement of intraluminal medical devices. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990s. Coronary and peripheral stents have been proven to provide a superior means of maintaining vessel patency, and have become widely accepted in the medical community. Furthermore, stents have been adapted for use in a variety of other treatments and medical devices.

Several researchers have pursued the development of prosthetic valves that are implantable by minimally invasive techniques over recent years. Indeed, the art now contains several examples of implantable cardiac and venous valve devices. Many of these prior art devices include an expandable support frame and an attached graft member that is fashioned into a valve that regulates fluid flow through the device and, ultimately, a body vessel. For example, a graft member can be in the form of a leaflet that is attached to a support frame and movable between first and second positions. In a first position, the valve is open and allows fluid flow to proceed through a vessel in a first direction, and in a second position the valve is closed to prevent fluid flow in a second, opposite direction. Examples of this type of prosthetic valve are described in commonly owned U.S. Pat. No. 6,508,833 to Pavcnik for a MULTIPLE-SIDED INTRALUMINAL MEDICAL DEVICE, United States Patent Application Publication No. 2001/0039450 to Pavcnik for an IMPLANTABLE VASCULAR DEVICE, and U.S. patent application Ser. No. 10/642,372, filed on Aug. 15, 2003, each of which is hereby incorporated by reference in its entirety. In other examples, a tube-like graft member that terminates in leaflets is used. The graft member is attached to one or more support frames to form a valve. The leaflets open to permit fluid flow in a first direction in response to fluid pressure on one side of the leaflets and close to prevent fluid flow in a second, opposite direction in response to fluid pressure on opposite sides of the leaflets. An example of this configuration is provided in U.S. Pat. No. 6,494,909 to Greenhalgh for AN ENDOVASCULAR VALVE, which is hereby incorporated by reference in its entirety.

Despite these and other examples, a need remains for improved implantable valve devices, methods of making such devices, and methods of treating various venous-related conditions, disorders and/or diseases.

SUMMARY OF EXEMPLARY EMBODIMENTS

Valve devices, methods of making valve devices, and methods of treating various venous-related conditions, disorders and/or diseases are described.

A valve device according to an exemplary embodiment of the invention comprises an expandable support frame and a bioprosthetic valve attached to the support frame. The bioprosthetic valve comprises a single leaflet harvested from a natural valve and a contiguous wall portion attached to the leaflet. In exemplary embodiments, the contiguous wall portion includes the portion of the vessel wall that defines the natural sinus for the leaflet. While the bioprosthetic valve can be harvested from any suitable source, the use of porcine valves, such as an aortic porcine valve, is considered advantageous.

The support frame is an expandable support frame that includes one or more struts. In exemplary embodiments, the support frame defines a window portion substantially free of the struts. The window portion is positioned such that the leaflet of the attached bioprosthetic valve is able to close against a portion of an inner wall of said recipient vessel.

In exemplary embodiments, the support frame defines an outwardly projecting portion configured to create a sinus region in the recipient vessel upon implantation therein.

A valve device according to one exemplary embodiment comprises a bioprosthetic valve comprising a single leaflet harvested from a donor valve and a contiguous wall portion, and an expandable support frame comprising one or more struts and defining an outwardly projecting portion configured to outwardly deflect a portion of the inner wall of the recipient vessel upon implantation therein. The bioprosthetic valve is attached to the support frame and, in this embodiment, the base portion of the leaflet is positioned substantially adjacent the outwardly projecting portion such that a valve sinus region is formed between the outwardly deflected portion of the inner wall of the recipient vessel and the leaflet.

A valve device according to another embodiment comprises an expandable support frame comprising one or more struts, the support frame defining an outwardly projecting portion configured to create a sinus region in said recipient vessel upon implantation therein and a window portion substantially free of the one or more struts; and a bioprosthetic valve comprising a natural valve leaflet harvested from a donor valve and a contiguous wall portion. In this embodiment, the bioprosthetic valve is attached to the support frame such that the leaflet is positioned substantially opposite the window portion when the valve is in an open position. Advantageously, this structure allows the leaflet to substantially close against a portion of an inner wall of the recipient vessel.

A valve device according to another embodiment comprises an expandable support frame defining an outwardly projecting portion configured to create a sinus region in a recipient vessel upon implantation therein and a window portion substantially free of the one or more struts; and a bioprosthetic valve attached to the support frame. The bioprosthetic valve comprises a noncoronary leaflet and a contiguous wall portion harvested from a xenogeneic aortic valve. The device also includes at least one suture attaching the contiguous wall portion to the support frame along an attachment pathway and passing through only a partial thickness of the contiguous wall portion at at least one point on the attachment pathway. The bioprosthetic valve is attached to the support frame such that the leaflet is positioned substantially opposite the window portion when the valve is in an open position.

Methods of making valve devices are also described. A method according to an exemplary embodiment comprises the steps of fabricating a bioprosthetic valve and attaching the bioprosthetic valve to a support frame. In one exemplary method, the step of fabricating a bioprosthetic valve includes the steps of providing a suitable xenogeneic valve, selecting a suitable leaflet, and excising tissue from the valve to leave a contiguous wall portion attached to the selected leaflet that includes the natural margins of attachment where the leaflet attaches to the vessel wall. The method can also include a step of reducing the thickness of the contiguous wall portion, such as by shaving or by another suitable technique.

In an exemplary method of making a valve device, a leaflet associated with the noncoronary sinus, also known as the posterior aortic sinus, of a xenogeneic aortic valve is selected.

Delivery systems for percutaneously delivering a valve device to a desired point of treatment in a recipient vessel are also provided. An exemplary delivery system comprises an elongate member having a proximal end, a distal tip adapted for insertion into and navigation through a recipient vessel, and a length from the proximal end to the distal tip. The elongate member includes a device chamber into which an expandable medical device can be disposed. A sheath is disposed about the elongate member and over the device chamber, and is adapted to slidably move along the length of the elongate member. A valve devices according to an embodiment of the invention, such as the exemplary embodiment described above, is disposed within the device chamber.

Additional understanding can be obtained with review of the detailed description of exemplary embodiments, appearing below, and the appended drawings illustrating exemplary embodiments.

BRIEF DESCRIPTION OF THE DRAWINGS

FIG. 1A is a front perspective view of a bioprosthetic valve suitable for use in valve devices according to the invention.

FIG. 1B is a front perspective view of an alternate bioprosthetic valve suitable for use in valve devices according to the invention.

FIG. 1C is a front perspective view of an alternate bioprosthetic valve suitable for use in valve devices according to the invention.

FIG. 3 is a perspective view of a valve device according to a first exemplary embodiment.

FIG. 4 is an end view of the valve device illustrated in FIG. 3. The bioprosthetic valve of the device is shown in an open configuration.

FIG. 5 is an end view of the valve device illustrated in FIG. 3. The bioprosthetic valve of the device is shown in a closed configuration.

DETAILED DESCRIPTION OF EXEMPLARY EMBODIMENTS

Figure 2A:
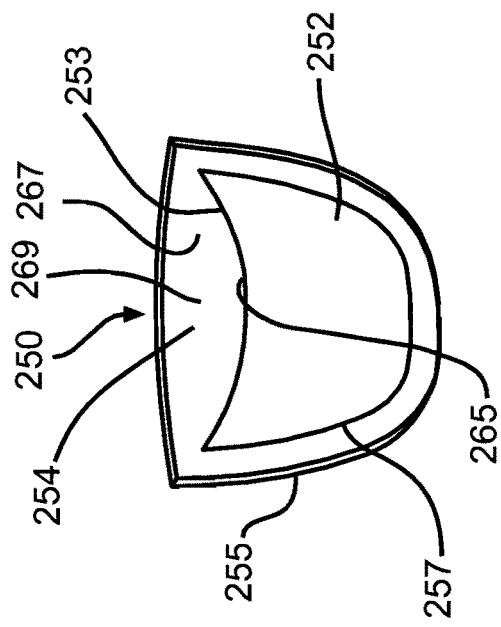
FIG. 2A is a front perspective view of an alternate bioprosthetic valve suitable for use in valve devices according to the invention.

The following detailed description and the appended drawings describe and illustrate various exemplary embodiments of the invention. The description and drawings are exemplary in nature and are provided to enable one skilled in the art to make and use one or more embodiments of the invention. They are not intended to limit the scope of the invention, or its protection, in any manner.

The invention provides implantable valve devices useful in regulating fluid flow through a body vessel of a patient, such as a human or other animal. Valve devices according to the invention include a bioprosthetic valve attached to a support frame.

As used herein, the term 'valve device' refers to an implantable medical device that includes a bioprosthetic valve attached to a support frame.

As used herein, the term 'bioprosthetic valve' refers to a valve comprising at least one leaflet and a contiguous wall portion harvested from a natural valve, such as a multi-leaflet vascular valve harvested from a xenogeneic source. The contiguous wall portion includes tissue taken from the natural valve at a natural attachment margin where the leaflet attaches to a vessel wall. The size and configuration of the contiguous wall portion varies between valve devices according to embodiments of the invention, as described below.

U.S. Non-provisional patent application Ser. No. 12/252,253, filed by Dr. Norman Jaffe of Dana Point, Calif. on Oct. 15, 2008, and entitled "BIOLOGICAL VALVE FOR VENOUS VALVE INSUFFICIENCY," describes various bioprosthetic valves suitable for use in valve devices according to the invention. The entire contents of this application are hereby incorporated into this disclosure for the purpose of describing suitable bioprosthetic valves, and their preparation, for inclusion in valve devices according to embodiments of the invention.

FIGS. 1A, 1B, and 1C illustrate three different bioprosthetic valves suitable for use in valve devices according to embodiments of the invention. The illustrated bioprosthetic valves are described fully in the incorporated 60/980,708 application and will only be described briefly herein. In each bioprosthetic valve illustrated in these Figures, the contiguous wall portion comprises a patch of tissue that extends axially, with respect to the source vessel and host vessel, above and below the leaflet and laterally on both sides of the leaflet. Use of this type of bioprosthetic valve might be advantageous in valve devices according to particular embodiments of the invention.

The bioprosthetic valve 100 illustrated in FIG. 1A includes a single leaflet 102 attached to a patch 104 of tissue at attachment region 106. The leaflet 102 has a free edge 103 which moves in response to differing pressures in the body vessel in which the bioprosthetic valve 100 is disposed to open and close the valve 100.

The patch 104 extends axially (with respect to the source vessel and host vessel) above and below the leaflet 102 to provide upper and lower regions 108(a), 108(b) for attaching the bioprosthetic valve 100 to a support frame in a valve device according to embodiments of the invention, as described below. If the bioprosthetic valve is from an aortic valve source, the patch 104 may include a segment of the aortic annulus and/or a segment of the aortic wall.

The patch 104 also extends circumferentially on either side of the leaflet 102 to provide lateral regions 110(a), 110(b) for attaching the bioprosthetic valve 100 to a support frame in a valve device according to embodiments of the invention, as described below. The regions 110(a), 110(b) may extend only minimally beyond the region of the leaflet 102, as shown in FIG. 1, or may extend further so as to partially or entirely encircle a circumferential support frame to which the bioprosthetic valve 100 is attached and a body vessel into which the bioprosthetic valve 100 is disposed. It is noted that, while the contiguous wall portion 104 extends in circumferential directions on either side of the leaflet 102, it advantageously does not extend to include a complete circumferential path on the circumference of the source vessel. Indeed, a contiguous wall portion comprising a non-circumferential portion of the source vessel wall is considered advantageous at least because it reduces the bulk of the resulting valve device, as described more fully below.

The patch 104 may be generally rectangular, as shown in FIG. 1, or may have any other suitable shape (such as circular, oval, or oblong). The specific shape chosen for the patch portion of the bioprosthetic valve in a valve device according to a particular embodiment of the invention will depend on various considerations, including the shape and/or configuration of the support frame included in the valve device. A skilled artisan will be able to select an appropriate shape for the patch based on these and/or other considerations.

It is noted that, while illustrated with the regions 108(a), 108(b) and 110(a), 110(b) extending substantially symmetrically above and below and on either side of the leaflet 102, the patch 104 can of course extend about the leaflet 102 by different lengths in different directions.

The bioprosthetic valve 100 and its leaflet 102 may be selected and configured so that, with the valve 100 attached to a support frame in a valve device, as described below, and in a closed position, the leaflet 102 provides adequate obstruction of the host body vessel at the point at which the valve device is disposed. The leaflet 102 need not, however, be selected or configured to completely obstruct the host body vessel in the closed position, as some degree of retrograde flow may be acceptable and even desirable. Accordingly, with the bioprosthetic valve 100 in a closed position, the free edge 103 of the leaflet 102 may (but need not) contact an opposing portion of an attached support frame and/or an opposing wall of the host body vessel, either partially or continuously along the length of the free edge 103.

The bioprosthetic valve 100 according to the embodiment illustrated in FIG. 1, and indeed all embodiments, may comprise tissue from any suitable xenogeneic source, such as porcine, bovine, or equine tissue. Porcine, bovine, and equine heart tissue is considered to be advantageous. Porcine heart tissue is considered particularly advantageous at least because of its ready availability and general acceptance as a suitable source of xenogeneic tissue. Also, the inventors have determined that the leaflets of porcine heart valves have sizes and configurations that render them suitable for use as venous valves in human patients.

FIG. 1B illustrates an alternative bioprosthetic valve 150 suitable for use in valve devices according to embodiments of the invention. The valve 150 has a single leaflet 152 attached to a patch 154 at attachment region 156 and has a free edge 153 that moves in response to differing pressures in the host body vessel to open and close the valve 150.

The patch 154 has a generally ovoid shape which extends axially (with respect to the source vessel and host vessel) above and below the leaflet 152 to provide upper and lower regions 158(a), 158(b) for attaching the bioprosthetic valve 150 to a support frame in a valve device according to embodiments of the invention, as described below. Similarly, the patch also extends circumferentially on either side of the leaflet 152, to provide lateral regions 160(a), 160(b) for attaching the bioprosthetic valve 150 to a support frame in a valve device according to embodiments of the invention, as described below.

FIG. 1C illustrates an alternative bioprosthetic valve 170 suitable for use in valve devices according to embodiments of the invention. The valve 170 has a single leaflet 172 attached to a patch 174 at attachment region 176 and has a free edge 173 that moves in response to differing pressures in the host body vessel to open and close the valve 170.

The patch 174 has a generally lenticular shape which extends axially (with respect to the source vessel and host vessel) above and below the leaflet 172 to provide upper and lower regions 178(a), 178(b) for attaching the bioprosthetic valve 170 to a support frame in a valve device according to embodiments of the invention, as described below. Similarly, the patch also extends circumferentially on either side of the leaflet 172, to provide lateral regions 180(a), 180(b) for attaching the bioprosthetic valve 170 to a support frame in a valve device according to embodiments of the invention, as described below. As shown in the Figure, the upper and lower regions 178(a), 178(b) may include pointed or angled sections to facilitate attachment of the bioprosthetic valve 170 to a support frame and/or a body vessel into which a valve device including the bioprosthetic valve is disposed.

FIGS. 2A, 2B, 2C, and 2D illustrate three alternate bioprosthetic valves suitable for use in valve devices according to embodiments of the invention. In each bioprosthetic valve illustrated in these Figures, the contiguous wall portion comprises a section of tissue having a lateral edge that extends along a path similar to the contour of an interface between the leaflet and contiguous wall portion. Also, the contiguous wall portion extends slightly beyond the interface to include the natural margins of attachment between the leaflet and vessel wall.

The bioprosthetic valve 200 illustrated in FIG. 2A includes a single leaflet 202 attached to a contiguous wall portion 204 having an outer edge 205 that extends along a path similar to the contour of the interface 207 between the leaflet 202 and contiguous wall portion 204. The leaflet 202 has a free edge 203 that moves in response to differing pressure in the body vessel in which the bioprosthetic valve 200 is disposed. This movement of the free edge 203 of the leaflet 202 effects opening and closing of the valve 200. In this embodiment, an inner surface 215 of the leaflet 202 and an inner surface 217 of the contiguous wall portion 204 define a valve pocket 220 that opens and closes as the free edge 203 moves.

In this embodiment, the contiguous wall portion 204 extends to substantially the same axial height, with respect to the source and host vessels, as the free edge 203 of the leaflet 202. This configuration of the contiguous wall portion 204 is considered advantageous at least because it provides a fixed tissue surface for the leaflet 203 to interact with as it moves and avoids interaction with the natural wall of the host vessel, which may be diseased and/or weakened.

Figure 2B:
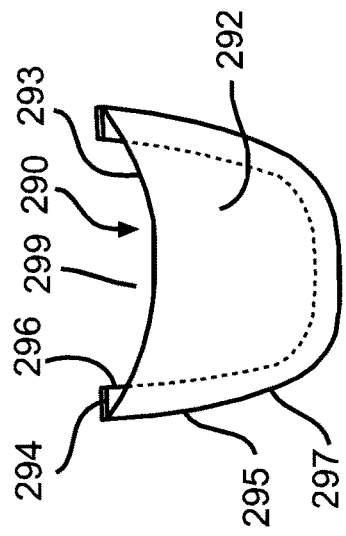
FIG. 2B is a front perspective view of an alternate bioprosthetic valve suitable for use in valve devices according to the invention.

The bioprosthetic valve 250 illustrated in FIG. 2B is similar to the valve 200 illustrated in FIG. 2A, except as described below. Thus, the valve 250 has a single leaflet 252 attached to a contiguous wall portion 254 having an outer edge 255 that extends along a path similar to the contour of the interface 257 between the leaflet 252 and contiguous wall portion 254. The leaflet 252 has a free edge 253 that moves in response to differing pressure in the body vessel in which the bioprosthetic valve 250 is disposed. In this embodiment, an inner surface 265 of the leaflet 252 and an inner surface 267 of the contiguous wall portion 254 define a valve pocket 269 that opens and closes as the free edge 253 moves.

In this embodiment, the contiguous wall portion 254 extends beyond the axial height of the free edge 253 of the leaflet 252. This configuration is considered advantageous at least because it provides the fixed tissue surface for the leaflet to interact with, as in the embodiment illustrated in FIG. 2A, but also provides an additional fixed tissue portion above the free edge 253 which may help to avoid fluid flow that passes behind the wall portion 254 when the leaflet 252 closes. Furthermore, the contiguous wall portion 254 in this embodiment includes substantially all of the tissue that defines the natural sinus for the leaflet 252. This is considered advantageous at least because the inclusion of the natural sinus facilitates flushing of the valve pocket 269 formed in the valve device 200, which is expected to enhance overall performance of the device 200.

Figure 2C:
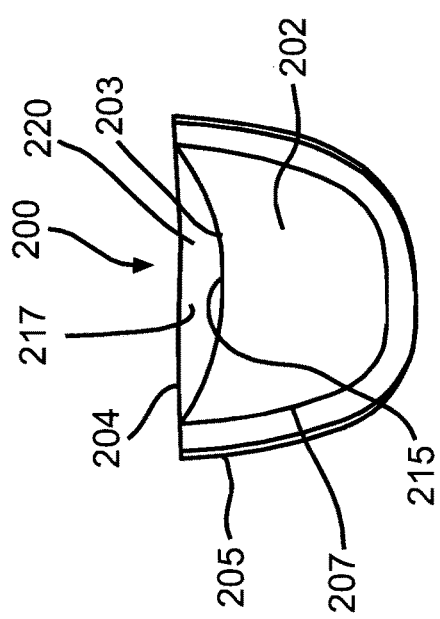
FIG. 2C is a front perspective view of an alternate bioprosthetic valve suitable for use in valve devices according to the invention.

The bioprosthetic valve 270 illustrated in FIG. 2C is similar to the valve illustrated in FIG. 2A, except as described below. Thus, the valve 270 has a single leaflet 272 attached to a contiguous wall portion 274 having an outer edge 275 that extends along a path similar to the contour 277 of the interface between the leaflet 272 and contiguous wall portion 274. The leaflet 272 has a free edge 273 that moves in response to differing pressure in the body vessel in which the bioprosthetic valve 270 is disposed. In this embodiment, an inner surface 285 of the leaflet 272 cooperatively defines a valve pocket 289 with an inner surface of the host vessel wall. The pocket 289 opens and closes as the free edge 273 moves.

In this embodiment, the contiguous wall portion 274 comprises a substantially U-shaped section of tissue that includes the natural margins of attachment between the leaflet 272 and wall portion 274 and extends only slightly beyond the interface between the leaflet 272 and wall portion 274. This configuration is considered advantageous at least because it retains the natural attachment margins between the leaflet 272 and the vessel wall, which has advantages, as described below, while minimizing the overall amount of tissue included in the valve 270. This may minimize the bulk associated with a valve device that includes the bioprosthetic valve 270.

Figure 2D:
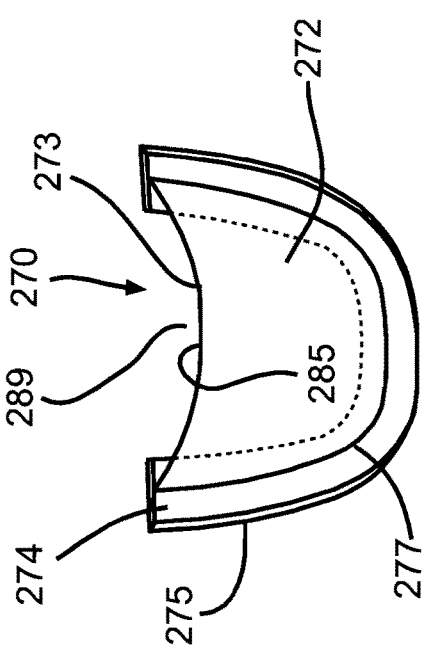
FIG. 2D is a front perspective view of an alternate bioprosthetic valve suitable for use in valve devices according to the invention.

The bioprosthetic valve 290 illustrated in FIG. 2D is similar to the valve illustrated in FIG. 2A, except as described below. Thus, the valve 290 has a single leaflet 292 attached to a contiguous wall portion 294 having an outer edge 295 that extends along a path similar to the contour 297 of the interface between the leaflet 292 and contiguous wall portion 294. The leaflet 292 has a free edge 293 that moves in response to differing pressure in the body vessel in which the bioprosthetic valve 290 is disposed. In this embodiment, an inner surface 298 of the leaflet 292 cooperatively defines a valve pocket 299 with an inner surface of the host vessel wall. The pocket 299 opens and closes as the free edge 293 moves.

In this embodiment, the contiguous wall portion 294 comprises a substantially U-shaped section of tissue that extends into the valve pocket 299 but that does not extend beyond the contour 297 of the interface between the leaflet 292 and contiguous wall portion 294. While this configuration may not include the complete margins of attachment between the leaflet 292 and the contiguous wall portion 294, it provides a bioprosthetic valve 290 having less bulk than the other embodiments, which may be desirable in situations in which the overall circumference of a valve device is a point of concern, such as valve devices intended for delivery through and/or implantation in body vessels having small inner diameters as compared to other body vessels.

In all embodiments, the inclusion of a contiguous wall portion that includes tissue taken from the donor vessel wall at an attachment region where the leaflet attaches to the vessel wall is considered advantageous at least because the attachment region includes a unique microstructure that is believed to enhance the ruggedness of the bioprosthetic valve in an implantable valve device. Retaining the natural margins of attachment between the leaflet and vessel wall in the contiguous wall portion is considered particularly advantageous. For example, in an aortic valve, the margins of attachment, i.e., the leaflet anchorages, are composed nearly exclusively of a dense collagenous tissue that provides a durable attachment between the leaflet and wall, which is expected to have a beneficial advantage on the longevity of a valve device that includes a bioprosthetic valve that includes the margins of attachment.

Valve devices according to embodiments of the invention also include a support frame. A wide variety of support frames are known in the medical technology arts, and any suitable support frame can be utilized in a valve device according to an embodiment of the invention. The support frame need only provide a surface to which the bioprosthetic valve can be attached in a manner that allows the valve to function as described herein. It is understood that the support frame need not have any particular structure and/or configuration and, indeed, can comprise minimal structure or distinct and independent structures attached to the bioprosthetic valve. For example, a support structure comprising one or more barbs or microbarbs, known to those skilled in the art of intraluminal medical devices, can be attached to the bioprosthetic valve and function as a support frame as contemplated herein.

As described below, the support frame advantageously comprises an expandable support frame having radially compressed and radially expanded configurations. Such a support frame can be implanted at a point of treatment within a body vessel by minimally invasive techniques, such as delivery and deployment with an intravascular catheter. It is noted, though, that valve devices according to embodiments of the invention, regardless of the type and/or nature of the support frame, can be implanted by other techniques, including surgical techniques.

The support frame can optionally provide additional function to the medical device. For example, the support frame can provide a stenting function, i.e., exert a radially outward force on the interior wall of a vessel in which the medical device is implanted. By including a support frame that exerts such a force, a valve device according to the invention can provide both a stenting and a valving function at a point of treatment within a body vessel, which may be desirable in certain situations, such as when a degree of vessel stenosis, occlusion, and/or weakening is present. A frame that provides an initial stenting function that decreases over time can also be used. Examples of such support frames are described in United States Patent Application Publication No. 20050228486 A1, entitled IMPLANTABLE FRAME WITH VARIABLE COMPLIANCE, the entire contents of which are hereby incorporated into this disclosure for the purpose of describing suitable support frames for use in valve devices according to the invention.

The stent art provides numerous support frames acceptable for use in the present invention, and any suitable stent can be used as the support frame. The specific support frame chosen will depend on numerous factors, including the body vessel in which the valve device is being implanted, the axial length of the treatment site within the vessel, the inner diameter of the vessel, the delivery method for placing the medical device, and other considerations. Those skilled in the art can determine an appropriate support frame for use in a specific valve device according to a particular embodiment based on these and other considerations as they exist in a particular body vessel and/or at a particular point of treatment. For example, for a point of treatment at which primary venous insufficiency is determined, a valve device with minimal support frame structure and minimal outwardly-directed radial force, such as the attached barbs and microbarbs described above, may be desirable and/or suitable. Other points of treatment, such a those at which a vessel wall has become weakened, damaged, or both, may require substantial support frame structure and/or outwardly-directed radial force, such as that provided by a support frame capable of serving a stenting function.

Both self-expandable support frames and support frames requiring an input of force to effect expansion, such as balloon expandable support frames, can be used in valve devices according to the invention. The structural characteristics of both of these types of support frames are known in the art, and are not detailed herein. Each type of support frame has advantages and for any given application, one type may be more desirable than other types based on a variety of considerations. For example, in the peripheral vasculature, vessels are generally more compliant and typically experience dramatic changes in their cross-sectional shape during routine activity. Medical devices for implantation in the peripheral vasculature should retain a degree of flexibility to accommodate these changes of the vasculature. Accordingly, valve devices according to the invention intended for implantation in the peripheral vasculature, such as valve devices, advantageously include a self-expandable support frame. These support frames, as is known in the art, are generally more flexible than balloon-expandable support frames following deployment.

Suitable support frames can be made from a variety of materials and need only be biocompatible or able to be made biocompatible. Examples of suitable materials include, without limitation, stainless steel, nickel titanium (NiTi) alloys, e.g., nitinol, other shape memory and/or superelastic materials, molybdenum alloys, tantalum alloys, titanium alloys, precious metal alloys, nickel chromium alloys, cobalt chromium alloys, nickel cobalt chromium alloys, nickel cobalt chromium molybdenum alloys, nickel titanium chromium alloys, linear elastic Nitinol wires, polymers, and composite materials. Also, resorbable and bioremodellable materials can be used. As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; trimethlyene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

Stainless steel and nitinol are currently considered desirable materials for use in the support frame due at least to their biocompatibility, shapeability, and well-characterized nature. Also, cold drawn cobalt chromium alloys, such as ASTM F562 and ASTM F1058 (commercial examples of which include MP35N™ and Elgiloy™, both of which are available from Fort Wayne Metals, Fort Wayne, Ind.; MP35N is a registered trademark of SPS Technologies, Inc. (Jenkintown, Pa., USA); Elgiloy is a registered trademark of Combined Metals of Chicago LLC (Elk Grove Village, Ill., USA)), are currently considered advantageous materials for the support frame at least because they are non-magnetic materials that provide beneficial magnetic resonance imaging (MRI) compatability, and avoid MRI artifacts typically associated with some other materials, such as stainless steel.

Suitable support frames can also have a variety of shapes and configurations, including braided strands, helically wound strands, ring members, consecutively attached ring members, zig-zag members, tubular members, and frames cut from solid tubes.

Examples of suitable support frames for use in medical devices according to the invention include those described in U.S. Pat. No. 6,464,720 to Boatman et al. for a RADIALLY EXPANDABLE STENT; U.S. Pat. No. 6,231,598 to Berry et al. for a RADIALLY EXPANDABLE STENT; U.S. Pat. No. 6,299,635 to Frantzen for a RADIALLY EXPANDABLE NON-AXIALLY CONTRACTING SURGICAL STENT; U.S. Pat. No. 4,580,568 to Gianturco for a PERCUTANEOUS ENDOVASCULAR STENT AND METHOD FOR INSERTION THEREOF; and published applications for United States Patent 20010039450 to Pavcnik et al. for an IMPLANTABLE VASCULAR DEVICE, 20040260389 to Case et al. for ARTIFICIAL VALVE PROSTHESIS WITH IMPROVED FLOW DYNAMICS; 20070038291 TO Case et al. for INTRALUMINALLY-IMPLANTABLE FRAMES; 20070162103 to Case et al. for IMPLANTABLE DEVICE WITH REMODELLABLE MATERIAL AND COVERING MATERIAL; 20070100435 to Case et al. for ARTIFICIAL PROSTHESIS WITH PREFERRED GEOMETRIES; and 20070021826 to Case et al. for INTRALUMINALLY IMPLANTABLE FRAMES, each of which is hereby incorporated by reference in its entirety for the purpose of describing suitable support frames for use in medical devices according to the invention.

The inclusion of a support frame in the valve devices according to embodiments of the invention is considered advantageous at least because it facilitates anchoring of the valve device at a point of treatment in a body vessel. Additionally, the support frame is believed to aid in placing the bioprosthetic valve in a beneficial 3D configuration that assists the valve device in achieving the benefits provided by the bioprosthetic valve.

The embodiments illustrated in FIGS. 3 through 8 include support frames having particularly advantageous structural features.

FIGS. 3 through 5 illustrate a valve device 300 according to a first exemplary embodiment. The valve device 300 includes a support frame 310 and a bioprosthetic valve 312 attached to the support frame 310.

Support frame 310 is described in detail in U.S. Pat. No. 6,508,833 to Pavcnik et al. for a MULTIPLE-SIDED INTRALUMINAL MEDICAL DEVICE, which is hereby incorporated by reference in its entirety for the purpose of describing suitable support frames for use in valve devices according to the invention. This support frame 310 is described briefly herein as an example of a suitable support frame for use in valve devices according to the invention.

The support frame 310 is made of resilient material, preferably metal wire formed from stainless steel or a superelastic alloy, such as nitinol. While round wire is depicted in the figures, other types, such as flat, square, triangular, D-shaped, and delta-shaped wire, may be used to form the frame 310. In the illustrated embodiment, the frame 310 comprises a single strut 314 configured into a closed circumference 316. The closed circumference 316 includes four sides 318, 320, 322, 324 of approximately equal length. Alternative embodiments include frames with sides of different lengths, and frames of any polygonal shape, such as pentagon, hexagon, and octagon shapes.

The sides 318, 320, 322, 324 are interconnected by bends, each of which can comprise a coil 326 in the material of the support frame 310, or a simple bend 328. Alternative bend embodiments include outward-projecting fillets and inward-projecting fillets comprising a series of curves. Fillets are well known in the stent art as a means for reducing stresses in bends.

The cross-sectional diameter of the wire selected will depend on the size of the medical device and the application. Wire that is too stiff can damage the vessel, not conform well to the vessel wall, and increase the profile of the device when loaded in a delivery system prior to deployment. Wire that is not sufficiently stiff may not allow the valve leaflet to function as desired. Furthermore, excessive outwardly-directed radial force may not be desirable in certain situation and/or at points of treatment having certain characteristics, as described above. The specific wire selected for a particular embodiment will depend on these and other considerations. Advantageously, the wire selected will provide the desired attachment to the bioprosthetic valve 312 and will allow a positive healing response to occur in the surrounding tissue or at least not inhibit such a response.

The single piece of material comprising the frame 310 is formed into the closed circumference 316 by securing the first and second ends 330, 332 with an attachment mechanism 334, such as a metal cannula. The ends 330, 332 are inserted into the cannula 334 and secured with a bonding element, such as solder, an adhesive, or other suitable bonding element. Also, a mechanical bond can be formed between the ends 330, 332 and attachment mechanism 334 by crimping, deformation of adjacent elements, or any other suitable technique. Also, the ends 330, 332 can be joined directly to each other without addition of an attachment mechanism, such as by soldering, welding, or other suitable methods to join material. Also alternatively, the frame 310 can be fabricated as a single piece of material by stamping or cutting a pattern from a sheet such as with a laser, fabricating from a mold, or some similar method of producing a unitary frame. Furthermore, the support frame 310 can be constructed to include structural elements that facilitate attachment and securement of the bioprosthetic valve 312 to the support frame 310, such as hooks, barbs, microbarbs, and other means for attaching tissue to a support frame, as is currently known or hereinafter developed.

When deployed in a lumen of a vessel, the support frame 310 exerts a radially outward force on the interior wall of the vessel. The bending stresses introduced to the frame 310 apply force radially outward against the vessel wall to hold the frame 310 in place and prevent vessel closure.

The bioprosthetic valve 312 includes a single leaflet 350 and a contiguous wall portion 352 of adjoining tissue. The leaflet 350 is attached to the contiguous wall portion 352 at attachment region 354. A free edge 356 of the leaflet 350 moves in response to differing pressures in the body vessel in which the bioprosthetic valve is disposed to effect opening and closing of the bioprosthetic valve 312.

In this embodiment, the bioprosthetic valve 312 is attached to the support frame by a suture 358 that extends along the entire length of the outer edge of the contiguous wall portion 352. While not illustrated in the Figures, additional connecting struts can be included in the support frame 310 to provide a full attachment path that extends along the entire outer edge of the contiguous wall portion 352 of the bioprosthetic valve 312.

The suture 358 advantageously comprises a single suture with no breaks or other interruptions along its length. The use of a single suture is considered advantageous at least because it avoids the presence of unnecessary knots, breaks and other structures that may present an impediment to fluid flow in a body vessel in which the valve device 300 is implanted. It is noted, though, that multiple sutures may be used and, indeed, may be desirable in valve devices according to particular embodiments.

Also advantageously, the suture 358 extends through only a partial thickness of the contiguous wall portion 352 in at least one pass through the contiguous wall portion 352. In particular embodiments, the suture 358 is exposed on the external surface of the bioprosthetic valve 310 but, because it passes only through a partial thickness of the contiguous wall portion 352, is not exposed on the internal surface of the valve 310. This is considered advantageous at least because it eliminates potential structure that may present an impediment to fluid flow and because it reduces the potential for thrombus formation on the internal surfaces of the valve 310, which is exposed to the blood when the valve device 300 is implanted in a body vessel. It is considered particularly advantageous to have the suture 358 extend through only a partial thickness of the contiguous wall portion 352 in substantially all of the passes through the contiguous wall portion 352. Currently, it is considered most advantageous to have the suture 358 extend through only a partial thickness of the contiguous wall portion 352 in all of the passes through the contiguous wall portion 352.

While FIGS. 3 through 5 illustrate a suture 358, it is noted that any suitable attachment element or means for attaching tissue to a support frame can be used to attach the bioprosthetic valve 312 to the support frame 310, including clips, adhesives, tissue solder, and other suitable structures, compositions, and techniques known in the art or hereinafter developed.

FIG. 4 illustrates the valve device 300 in an open configuration. In this configuration, the free edge 356 of the leaflet 350 has moved toward the contiguous wall portion 352, essentially collapsing against it and creating an open space 360 within the valve device 300. The open space 360 provides an open flow path in a body vessel when the valve device 300 is implanted therein.

FIG. 5 illustrates the valve device 300 in a closed configuration. In this configuration, the free edge 356 of the leaflet 350 has moved away from the contiguous wall portion 352 in response to a pressure change and/or flow reversal. In this embodiment, the leaflet 350 and an inner portion 370 of the contiguous wall portion 352 define a valve pocket 380. When the valve device 300 is in this configuration, the valve pocket 380 collects fluid and substantially prevents flow through the valve device 300, and through the body vessel, in the reverse, or antegrade, direction. It is noted that complete prevention of reverse fluid flow is not necessary for the valve device 300 to function properly and, as described above, the desired degree of prevention can be optimized by selection of an appropriate leaflet 350 with a size that will enable the desired degree of valve closure in operation.

Figure 6:
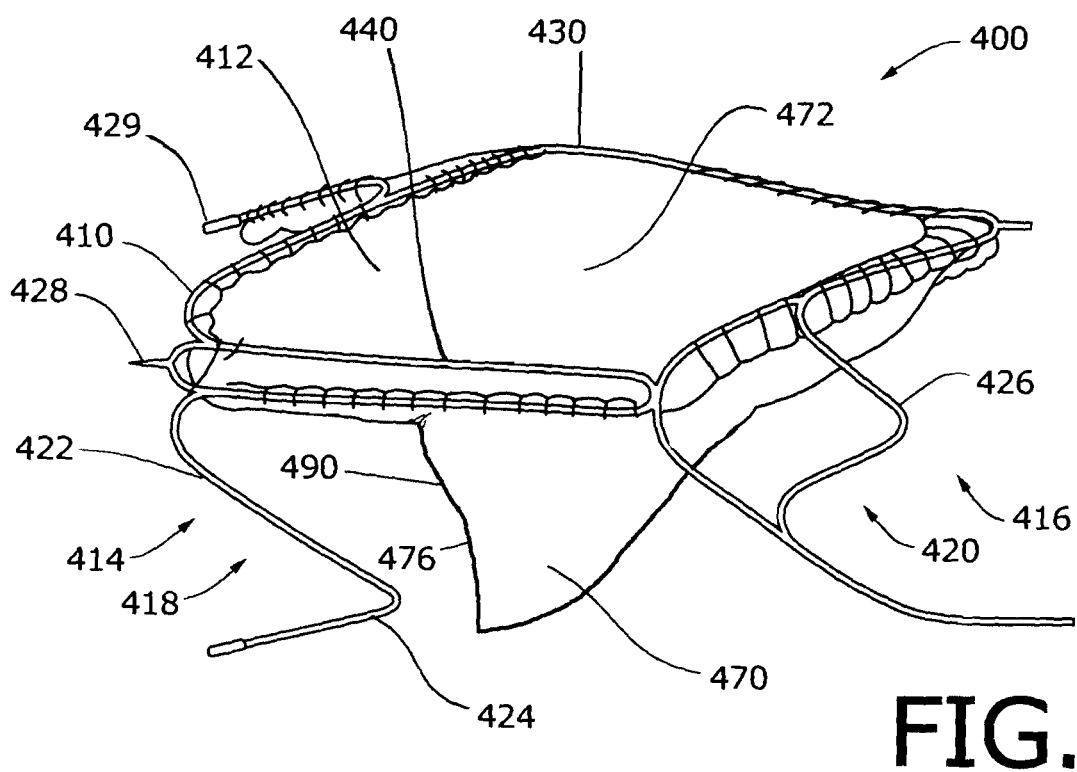
FIG. 6 is a side view of a valve device according to a second exemplary embodiment.
Figure 7:
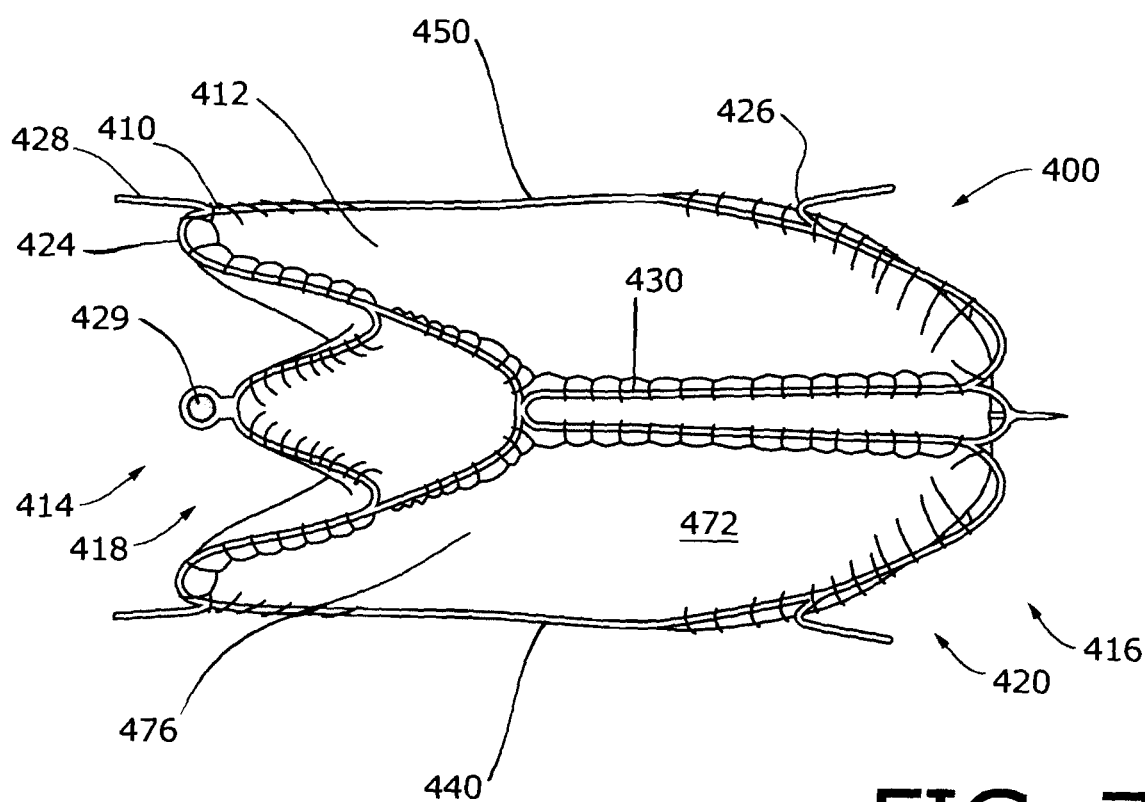
FIG. 7 is a top view of the valve device illustrated in FIG. 6.

FIGS. 6 and 7 illustrate a valve device 400 according to a second exemplary embodiment. The valve device 400 includes a support frame 410 and a bioprosthetic valve 412 attached to the support frame 410.

The support frame 410 is a self-expandable support frame comprising proximal 414 and distal 416 portions connected by various connector segments 430, 440. The proximal portion 414 defines a first serpentine path 418 that extends around the circumference of the support frame 410. The distal portion 416 defines a second serpentine path 420 that also extends around the circumference of the support frame 410. Each serpentine path 418, 420 includes straight strut portions 422 that are interconnected by bends 424. Each serpentine path also includes secondary bends 426 that substantially mirror bends 424 on the path. The support frame 410 advantageously includes conventional structural features that facilitate anchoring, such as barbs 428, and structural features, such as radiopaque markers 429, that facilitate visualization of the valve device 400 in conventional or other medical visualization techniques, such as radiography, fluoroscopy, and other techniques.

In the illustrated embodiment, each of the connector segments 430, 440 include first and second struts that are substantially straight and disposed substantially parallel to each other. This arrangement of struts in the connector segments 430, 440 is considered advantageous at least because it provides a degree of structural redundancy and gives a secondary attachment point for the bioprosthetic valve 412 along the length of the connector segments 430, 440. In embodiments in which the means for attaching the bioprosthetic valve 412 to the support frame 410 extends through only a partial thickness of the tissue of the bioprosthetic valve, this secondary attachment point can be used at any point along the length of the segments 430, 440 when a first attempt to pass through a partial thickness of the tissue is unsuccessful. The inventors have discovered that this is particularly advantageous in valve devices in which the bioprosthetic valve is attached to the support frame using one or more sutures 480.

In the illustrated embodiment, one connector segment 430 defines an outwardly-projecting curve. When the valve device 400 is implanted in a body vessel, the curve forces a part of the vessel wall outward, which defines a sinus at the point of implantation. This structural feature is considered advantageous at least because the provision of a sinus is believed to aid in the opening and closing of the bioprosthetic valve 412 by creating flow patterns that facilitate movement of the free edge 476 of the leaflet 470, which may enhance the overall performance of the valve device 400. It is believed to be advantageous to attach the contiguous wall portion 472 of the bioprosthetic valve 412 to the connector segment 430 defining the outwardly projecting curve. It is believed to be particularly advantageous to form a continuous attachment between the contiguous wall portion 472 and the connector segment 430 defining the outwardly projecting curve, such as by suturing along the length of the curve and/or connector segment, at least because this is expected to ensure a more complete definition of the sinus region in the valve device 400 and to enhance securement of the bioprosthetic valve 412 to the support frame 410.

The embodiment illustrated in FIGS. 6 and 7 include a support frame 410 having three connector segments 430, 440, 450. Connector segment 430 defines the curve, as described above, and is disposed substantially opposite to the inside surface of the leaflet 470 of the bioprosthetic valve 412. Connector segments 440, 450 are disposed substantially opposite to each other and near the attachment region 474 at which the leaflet 470 is attached to the contiguous wall portion 472. Also, as best illustrated in FIG. 8, connector segments 440, 450 lack a curve and are disposed substantially parallel to each other. This structural arrangement ensures that the valve pocket formed when the bioprosthetic valve 412 is in the closed configuration is not shallowly formed and that the leaflet 470 is able to sealingly interact with the vessel wall.

As best illustrated in FIG. 6, the underside of the support frame 410, which represents the side disposed substantially opposite an exterior surface 478 of the leaflet 470, lacks a connector segment. Instead, this side of the support frame 410 is largely open. This structural arrangement is considered advantageous at least because it enables the free edge 476 of the leaflet 470 to interact with the vessel wall during closure of the bioprosthetic valve 412, which is believed to result in better sealing and prevention of fluid flow in the reverse direction when the bioprosthetic valve 412 is in the closed configuration. This configuration is also expected to minimize wear of the leaflet edge 476 because it avoids abrasion that might result if the edge 476 were allowed to interact with a portion of the support frame 410.

It is noted that, while the illustrated support frame 410 includes three connector segments 430, 440, 450, any suitable number can be used and the specific number chosen for a particular valve device according to an embodiment of the invention will depend on various considerations, including the nature and size of the bioprosthetic valve 412 and the nature and size of the body vessel into which the valve device is intended to be implanted. Also, while the illustrated connector segments are disposed substantially equidistant from each other, it is noted that any suitable arrangement can be used and the specific arrangement chosen for a particular valve device according to an embodiment of the invention will depend on various considerations, including the nature and size of the bioprosthetic valve 412 and the nature and size of the contiguous wall portion 472 of the valve 412.

In the embodiments illustrated in FIGS. 6 and 7, the bioprosthetic valve 412 is attached to the support frame 410 in a manner such that the valve is normally open, i.e., the free edge 476 of the leaflet 470 is collapsed against the contiguous wall portion, thereby allowing fluid flow to pass through the lumen of the valve device 400 and the vessel in which it is implanted. As best illustrated in FIG. 6, the valve 410 closes only when a pressure head develops on an antegrade side of the valve 410 that is sufficient to force the free edge 476 of the leaflet 470 away from the contiguous wall portion 472 and adjacent wall of the body vessel and toward, and potentially against, the opposing wall of the body vessel. In this configuration, a valve pocket 490 is formed that fills with fluid until the valve 410 returns to its open configuration, which can occur in response to a change in the fluid pressure differential across the valve 410, a change in fluid flow direction, or both.

It is noted that, although the embodiments illustrated in FIGS. 3 through 7 include a single leaflet, it is expressly understood that a bioprosthetic valve having two or more leaflets can be used in the valve devices according to the invention. For example, for valve devices intended to be used in body vessels having relatively large internal diameters (e.g., vessels with diameters greater than 16 mm, such as adult human jugular and iliac veins), it may be advantageous to use a bioprosthetic valve that includes two or more leaflets attached to a contiguous wall portion. In these embodiments, the contiguous wall portion need not include any commissure(s) between the leaflets. Multi-leaflet bioprosthetic valves are advantageously attached to the support frame such that the free edges of the leaflets are able to coapt with each other such that the leaflets can close a valve opening formed inside the lumen of the valve device. A multi-leaflet bioprosthetic valve can be prepared from a single, xenogeneic valve having multiple leaflets by excising two or more leaflets from the valve while retaining a contiguous wall portion with the leaflets. The resulting bioprosthetic valve can then be attached to a support frame as described to provide a valve device. Also, a bioprosthetic valve can comprise multiple leaflets selected from multiple xenogeneic valves that are attached to the support frame to form a valve device. In these embodiments, two or more leaflets, each having a contiguous wall portion, are selected from two or more xenogeneic valves. The leaflets are attached to a single support frame such that the free edges of the leaflets coapt in a manner that closes a valve opening formed between the leaflets. In these embodiments, each leaflet is advantageously a noncoronary leaflet, for reasons described below. For valve devices that include a multi-leaflet bioprosthetic valve and a support frame such as that illustrated in FIGS. 6 and 7, it is expected to be advantageous to eliminate the strutless window portion by including an additional connector segment, such as segments 430, 440, 450, in the frame and to position one or more additional sinus-defining structural features, such as connector segment 430, opposite the additional leaflets.

Methods of making valve devices suitable for implantation in a patient, such as a human or other animal, are also provided.

A first step of an exemplary method comprises fabricating a bioprosthetic valve. In one exemplary method, the fabrication is done in accordance with the method described in incorporated U.S. Non-provisional patent application Ser. No. 12/252,253. In this method, a xenogeneic valve is harvested and fixed using suitable techniques, such as by fixing the valve with gluteraldehyde or any other suitable cross-linking agent. Examples of suitable fixation techniques are described in U.S. Pat. No. 4,800,603 to Jaffe for TISSUE FIXATION WITH VAPOR; U.S. Pat. No. 5,595,571 to Jaffe and Hancock for BIOLOGICAL MATERIAL PRE-FIXATION TREATMENT; U.S. Pat. No. 5,720,777 to Jaffe and Hancock for BIOLOGICAL MATERIAL PRE-FIXATION TREATMENT; U.S. Pat. No. 5,843,180 to Jaffe and Hancock for METHOD OF TREATING A MAMMAL HAVING A DEFECTIVE HEART VALVE; and U.S. Pat. No. 5,843,181 to Jaffe and Hancock for BIOLOGICAL MATERIAL PRE-FIXATION TREATMENT, each of which is hereby incorporated by reference in its entirety for the purpose of describing suitable techniques for fixing a xenogeneic valve for inclusion in a valve device according to the disclosure.

The use of a fixed valve is considered advantageous at least because the fixation process renders the tissue resistant to thrombosis while maintaining desirable compliance and mechanical properties of the valve. The use of a fixed valve aids in the handling of the valve during the fabrication method and may also enhance the performance of the resulting valve device. A fabrication step in which a xenogeneic valve is first fixed by exposure to gluteraldehyde followed by an irradiation step is considered particularly advantageous at least because the resulting bioprosthetic valve is sterile and has desirable compliance properties.

Tissue processed using the same procedures used by Hancock-Jaffe Laboratories of Irvine, Calif., to fabricate prosthetic heart valves may be used in the fabrication of bioprosthetic valves for use in the methods and apparatuses of the present invention.

In an exemplary fabrication method, a suitable xenogeneic valve is provided and a suitable leaflet of the valve is selected based on various considerations, including the size and configuration of the vessel in which the valve device will be implanted. When a xenogeneic aortic valve, such as an aortic valve, is being used, selecting a leaflet that is associated with the noncoronary sinus, also known as the posterior aortic sinus, is considered advantageous at least because the wall portion contiguous with this leaflet does not include an opening to a vessel originating from the sinus.

While it is preferred to select a noncoronary leaflet, it is noted that a coronary sinus leaflet can be selected and used and, in some circumstances, may even be desired. For example, the opening can be closed using appropriate techniques. Alternatively, the opening can be used to provide an attachment point at which the contiguous wall portion can be attached to the host vessel, if desired.

Once a suitable leaflet is selected, tissue is excised and/or trimmed to leave a contiguous wall portion that includes the attachment region where the leaflet attaches to the vessel wall. As described above, the wall portion can comprise a minimal section of tissue, such as the portion illustrated in FIG. 2C, or a larger patch of contiguous tissue that extends axially and circumferentially beyond the leaflet. Any other suitable size and configuration can be used for the contiguous wall portion and a skilled artisan will be able to select an appropriate size and configuration based on various considerations, including the size of the valve device being made and the vessel in which the device is to be implanted. At a minimum, the wall portion should include the attachment region where the leaflet attaches to the vessel wall. As described above, it is considered particularly advantageous to retain the natural margins of attachment between the leaflet and the vessel wall in the contiguous wall portion.

In an optional step, the thickness of the contiguous wall portion can be reduced following harvesting and prior to attachment to a support frame. Any suitable technique for reducing tissue thickness can be used, including shaving, manual dissection, delamination, and other techniques. Use of this step is believed to be advantageous at least because it reduces the overall profile of the bioprosthetic valve, which can minimize bulk in the resulting valve device, and can provide a consistent thickness to the wall portion. If this step is used, at least the margins of attachment between the leaflet and vessel wall should be retained to provide the desirable microstructure located in these areas, as described above. Also, it is noted that it may be advantageous to reduce the thickness of one or more of the axial edges of the contiguous wall portion, with respect to the lengthwise axis of the body vessel within which the bioprosthetic valve is intended to be used, such that a tapered thickness is provided. The edges can be reduced to a minimal thickness that gradually tapers to a suitable thickness at the attachment region where the leaflet is attached to the contiguous wall portion which substantially retains the margins of attachment between the leaflet and wall portion. Reducing the thickness of the one or more axial edges of the contiguous wall portion in this manner is believed to be advantageous at least because it may remove one or more blunt edges that could provide a surface for clot formation or otherwise impede fluid flow once the bioprosthetic valve is positioned within a body vessel.

A second step of the exemplary method of making valve devices suitable for implantation in a patient comprises attaching the bioprosthetic valve to a support frame. In exemplary methods, the step attaching the bioprosthetic valve to a support frame is accomplished by connecting the bioprosthetic valve to the support frame using a single suture. In exemplary methods, a suture or other suitable means for attaching is caused to extend through only a partial thickness of the contiguous wall portion in at least one of the passes through the contiguous wall portion. In exemplary methods, the suture or other suitable means for attaching is caused to extend through only a partial thickness of the contiguous wall portion in substantially all of the passes through the contiguous wall portion. In exemplary methods, the suture or other suitable means for attaching is caused to extend through only a partial thickness of the contiguous wall portion in all of the passes through the contiguous wall portion.

Also, in exemplary methods, the contiguous wall portion advantageously is attached to the support frame along the entire outer edge of the contiguous wall portion. In exemplary methods, a substantially continuous attachment is formed along the entire outer edge of the contiguous wall portion. Also in exemplary methods, the contiguous wall portion is attached to a sinus-defining feature of the support frame, such as an outwardly-projecting curve or other structural feature. It is believed to be advantageous to form a continuous attachment between the contiguous wall portion and such a structural feature, such as by suturing the wall portion along substantially the entire length of the structural feature, or along the entire length of the structural feature at least because this is expected to ensure a more complete definition of the sinus region in the valve device and to enhance securement of the bioprosthetic valve to the support frame.

Another exemplary method of making a valve device suitable for implantation in a patient comprises the steps of excising a xenogeneic valve from a host; fixing the valve using a suitable fixation technique, such as exposing the valve to gluteraldehyde or other suitable fixative; attaching the valve to a suitable support frame; trimming the valve to form a bioprosthetic valve as described herein; placing the valve device in a suitable storage medium, such as physiological saline; and irradiating the valve device. It is noted that the step of trimming the excised valve can be conducted before or after the valve is attached to the support frame. Conducting this step before the valve has been attached to the support frame is considered advantageous at least because doing so eliminates potential interference by the frame during the trimming process.

The invention also provides methods of treating venous insufficiency. An exemplary method comprises the steps of providing a valve device according to an embodiment of the invention and implanting the valve device in a body vessel of a patient containing at least one insufficient natural valve. In exemplary methods, the implanting step is accomplished by percutaneously delivering the valve device to a point of treatment in the body vessel and deploying the valve device at the point of treatment. In these exemplary methods, the valve device is loaded into a suitable percutaneous delivery system, which is then used to delivery the valve device to the point of treatment within the body vessel at which the valve device is to be deployed and implanted. Any suitable percutaneous delivery system can be used, and the delivery system selected need only be able to accommodate the valve device in a compressed configuration and accomplish the desired delivery to the point of treatment within the body vessel. Conventional pusher-type delivery systems that include a pusher and/or dilator with a surrounding sheath and that define a chamber into which the valve device can be loaded for delivery are considered suitable. When selecting a delivery system, care should be taken to ensure that the delivery system can accommodate the bulk of the bioprosthetic valve when the valve device is loaded into the delivery system.

Other examples of suitable delivery systems include those described in United States Patent Application Publication No. 20080221656 to Hartley et al. for ENDOVASCULAR DEPLOYMENT DEVICE; 20070088424 to Greenberg et al. for ENDOLUMINAL DELIVERY ASSEMBLY; 20060004433 TO Greenberg et al. for THORACIC DEPLOYMENT DEVICE AND STENT GRAFT;

20040230287 to Hartley et al. for BRANCH STENT GRAFT DEPLOYMENT AND METHOD; 20040098079 to Hartley et al. for THORACIC AORTIC STENT GRAFT DEPLOYMENT DEVICE; AND 20030225446 to Hartley for MULTI-PIECE PROSTHESIS DEPLOYMENT APPARATUS, each of which is hereby incorporated by reference in its entirety for the purpose of describing suitable delivery systems for use with the valve devices described herein.

In other exemplary methods, the implanting step is accomplished by surgically placing the valve device at a point of treatment in a body vessel.

EXAMPLE

Hemodynamic Evaluation of Valve Device

To evaluate the hydrodynamic performance and leaflet motion characteristics of a venous valve device according to the disclosure, several valve devices of various sizes were constructed and tested in the aortic chamber of a pulsatile flow heart valve test apparatus. Hydrodynamic performance was observed under a range of conditions typical of the upper leg of a human being. Leaflet function (i.e., opening and closing) was confirmed for all valve devices under all test conditions studied.

a. Construction of Valve Devices

Three unconstrained diameters (10 mm, 12 mm, and 14 mm) believed to be suitable for valve devices intended to be implanted in a human vein were selected for evaluation. For each unconstrained diameter, three valve devices were constructed by attaching a gluteraldehyde crosslinked bioprosthetic valve to a support frame by suturing. All specimens were submerged in saline following construction and subjected to irradiation.

b. Simulation of Compression for Loading into Percutaneous Delivery System

All specimens were loaded into a delivery catheter as shown in the Table I, and held in the compressed delivery configuration for at least 60 (sixty) minutes prior to testing.

TABLE I

Valve device unconstrained diameters and delivery sheath
French size for simulation of loading compression

| Valve device unconstrained diameter (mm) | Delivery sheath French size (Fr) |
|---|---|
| 10 | 14 |
| 12 | 16 |
| 14 | 18 | c. Test System and Parameters

Each valve device evaluated in the aortic chamber of a pulsatile flow apparatus from ViVitro Systems, Inc. (Victoria, British Columbia, Canada). Each valve device was sutured into a section of silicone tubing sized so as not to constrain the valve device. Arterial pressure was adjusted to achieve the desired static pressure. Table II provides detailed conditions under which the pulsatile flow analysis was conducted for each valve device.

TABLE II

Pulsatile flow test conditions

| Parameter | Condition |
|---|---|
| Test solution | Physiological saline maintained at 37 ± 1° C. |
| Cycle rate | 30 bbm |
| Cardiac output | 1.2 L/min |
| Static pressure | 15 mmHG ± 1, 35 mmHG ± 1, 50 mmHg ± 1, 100 mmHG ± 1 |
| Single stroke wave form | 70% with leaflet in open position, 30% with leaflet in closed position | d. Results

The valve devices were observed and visually recorded on video taken from the outflow aspect of the valve device. Confirmation of opening and closing of the leaflet of each valve device was made through visual review of video recordings of the pulsatile flow test. Table III presents a summary of the visual confirmations.

TABLE III

Leaflet function based upon review of
video recording of pulsatile flow test

| | | Leaflet opening and closing confirmed | | | |
|---|---|---|---|---|---|
| Valve. device No | Diameter (mm) | 15 mmHG | 35 mmHG | 50 mmHg | 100 mmHg |
| 1 | 10 | yes | yes | yes | yes |
| 2 | 10 | yes | yes | yes | yes |
| 3 | 10 | yes | yes | yes | yes |
| 4 | 12 | yes | yes | yes | yes |
| 5 | 12 | yes | yes | yes | yes |
| 6 | 12 | yes | yes | yes | yes |
| 7 | 14 | yes | yes | yes | yes |
| 8 | 14 | yes | yes | yes | yes |
| 9 | 14 | yes | yes | yes | yes | e. Conclusion

Based on these results, it was concluded that the valve devices made in accordance with the disclosure and tested as detailed above demonstrated acceptable leaflet function over the range of hemodynamic conditions evaluated.

The foregoing detailed description provides exemplary embodiments of the invention and includes the best mode for practicing the invention. The description and illustration of embodiments is intended only to provide examples of the invention and not to limit the scope of the invention, or its protection, in any manner.

What is claimed is:

1. A support frame for implantation in a recipient vessel, said support frame having a longitudinal axis and comprising:
a first connector segment, a second connector segment, and a third connector segment, the first connector segment disposed substantially opposite the second connector segment with respect to said longitudinal axis, the first connector segment and the second connector segment substantially parallel to each other, the third connector segment disposed circumferentially between the first connector segment and the second connector segment with respect to said longitudinal axis, the third connector segment defining an outwardly-projecting curve extending away from the longitudinal axis; and
a proximal portion and a distal portion, the proximal portion and the distal portion connected by the first connector segment, the second connector segment, and the third connector segment;

wherein the outwardly-projecting curve extends from the proximal portion toward the distal portion and away from the longitudinal axis when implanted in said recipient vessel.

2. The support frame of claim 1, wherein the outwardly-projecting curve creates a sinus region when implanted in said recipient vessel.

3. The support frame of claim 1, further comprising a window portion free of a connector segment, the window portion disposed between the first connector segment and the second connector segment; and wherein the window portion is disposed substantially opposite the third connector segment.

4. The support frame of claim 1, wherein the third connector segment is disposed in a plane that contains the longitudinal axis.

5. The support frame of claim 1, wherein the proximal portion comprises a closed circumference; and wherein the distal portion comprises a closed circumference.

6. The support frame of claim 1, wherein the proximal portion and the distal portion comprise consecutively attached ring members.

7. The support frame of claim 1, wherein the first connector segment, the second connector segment, and the third connector segment are formed of a cobalt chromium alloy.

8. The support frame of claim 1, wherein the first connector segment, the second connector segment, and the third connector segment are formed from a flat wire.

9. The support frame of claim 1, wherein the first connector segment, the second connector segment, and the third connector segment are formed from a single piece of material.

10. A support frame for implantation in a recipient vessel, said support frame having a longitudinal axis and comprising:

a first connector segment, a second connector segment, and a third connector segment, the first connector segment disposed substantially opposite the second connector segment with respect to said longitudinal axis, the first connector segment and the second connector segment substantially parallel to each other, the third connector segment disposed circumferentially between the first connector segment and the second connector segment with respect to said longitudinal axis, the third connector segment defining an outwardly-projecting curve extending away from the longitudinal axis; and a proximal portion and a distal portion, the proximal portion and the distal portion connected by the first connector segment, the second connector segment, and the third connector segment;

wherein outwardly-projecting curve extends from the distal portion toward the proximal portion and away from the longitudinal axis when implanted in said recipient vessel.

11. The support frame of claim 10, wherein the outwardly-projecting curve creates a sinus region when implanted in said recipient vessel.

12. The support frame of claim 10, further comprising a window portion free of a connector segment, the window portion disposed between the first connector segment and the second connector segment; and wherein the window portion is disposed substantially opposite the third connector segment.

13. The support frame of claim 10, wherein the third connector segment is disposed in a plane that contains the longitudinal axis.

14. The support frame of claim 10, wherein the proximal portion comprises a closed circumference; and wherein the distal portion comprises a closed circumference.

15. The support frame of claim 10, wherein the proximal portion and the distal portion comprise consecutively attached ring members.

16. The support frame of claim 10, wherein the first connector segment, the second connector segment, and the third connector segment are formed of a cobalt chromium alloy.

17. The support frame of claim 10, wherein the first connector segment, the second connector segment, and the third connector segment are formed from a flat wire.

18. The support frame of claim 10, wherein the first connector segment, the second connector segment, and the third connector segment are formed from a single piece of material.

* * * * *